(12) United States Patent
Ohkubo et al.

(10) Patent No.: US 11,186,810 B2
(45) Date of Patent: Nov. 30, 2021

(54) CELL CULTURE VESSEL

(71) Applicants: Shimadzu Corporation, Kyoto (JP); Yokohama City University, Kanagawa (JP); Osaka University, Osaka (JP); CORNING INCORPORATED, Corning, NY (US)

(72) Inventors: Tomoki Ohkubo, Kyoto (JP); Masaki Kanai, Kyoto (JP); Hirohisa Abe, Kyoto (JP); Hideki Taniguchi, Kanagawa (JP); Masahiro Kinooka, Osaka (JP); Goro Kobayashi, Tokyo (JP); Takanori Takebe, Kanagawa (JP)

(73) Assignees: SHIMADZU CORPORATION, Kyoto (JP); YOKOHAMA CITY UNIVERSITY, Kanagawa (JP); OSAKA UNIVERSITY, Osaka (JP); CORNING INCORPORATED, Corning, NY (US)

( * ) Notice: Subject to any disclaimer, the term of this patent is extended or adjusted under 35 U.S.C. 154(b) by 282 days.

(21) Appl. No.: 16/084,283

(22) PCT Filed: Mar. 16, 2016

(86) PCT No.: PCT/JP2016/058409
§ 371 (c)(1),
(2) Date: Sep. 12, 2018

(87) PCT Pub. No.: WO2017/158777
PCT Pub. Date: Sep. 21, 2017

(65) Prior Publication Data
US 2019/0078044 A1   Mar. 14, 2019

(51) Int. Cl.
*C12M 1/00*   (2006.01)
*C12M 3/00*   (2006.01)
(Continued)

(52) U.S. Cl.
CPC ............. *C12M 23/16* (2013.01); *C12M 3/00* (2013.01); *C12M 29/00* (2013.01); *C12M 41/00* (2013.01); *C12M 41/44* (2013.01)

(58) Field of Classification Search
None
See application file for complete search history.

(56) References Cited

U.S. PATENT DOCUMENTS

| 5,372,712 A | 12/1994 | Petit |
| 2002/0197713 A1* | 12/2002 | Cadwell ................. C12M 27/16 435/325 |

(Continued)

FOREIGN PATENT DOCUMENTS

| CN | 103966095 A | 8/2014 |
| FR | 2499542 A1 | 8/1982 |

(Continued)

OTHER PUBLICATIONS

Japanese Office Action dated Jun. 9, 2020, in connection with corresponding JP Application No. 2018-505152 (10 pp., including machine-generated English translation).
(Continued)

*Primary Examiner* — Holly Kipouros
(74) *Attorney, Agent, or Firm* — Maier & Maier, PLLC

(57) ABSTRACT

A cell culture container includes a storage container, a cell culture area, a culture solution supply unit, and a discharge unit. The cell culture area is a region for culturing cells, and is provided in the storage container. The culture solution supply unit supplies the culture solution into the cell culture area at a flow rate equal to or less than a predetermined flow rate. The discharge unit discharges the liquid in the cell culture area to the outside of the storage container. A rectification unit is a structure in which a plurality of outflow ports are uniformly arranged in a direction perpendicular to the flow direction of the culture solution from the culture solution supply unit to the discharge unit.

4 Claims, 7 Drawing Sheets

(51) Int. Cl.
*C12M 3/06* (2006.01)
*C12M 1/34* (2006.01)

(56) References Cited

U.S. PATENT DOCUMENTS

| | | | |
|---|---|---|---|
| 2008/0085556 A1* | 4/2008 | Graefing | C12M 21/06 435/383 |
| 2013/0189770 A1 | 7/2013 | Wu et al. | |
| 2015/0322397 A1 | 11/2015 | Cornforth et al. | |
| 2017/0226462 A1 | 8/2017 | Wu | |

FOREIGN PATENT DOCUMENTS

| | | |
|---|---|---|
| JP | H06-319525 A | 11/1994 |
| JP | 2006-141326 A | 6/2006 |
| JP | 2010-022275 A | 2/2010 |
| JP | 2014-147342 A | 8/2014 |
| JP | 2015-519922 A | 7/2015 |
| WO | 2015/176653 A1 | 11/2015 |

OTHER PUBLICATIONS

Japanese Office Action dated Oct. 1, 2019, in connection with corresponding JP Application No. 2018-505152 (8 pgs., including machine-generated English translation).

Extended European Search Report dated Oct. 30, 2019, including the Supplementary European Search Report and the European Search Opinion, in connection with corresponding EP Application No. 16894395.9 (7 pgs.).

International Search Report with English translation and Written Opinion dated May 24, 2016 of corresponding International Application No. PCT/JP2016/058409; 7 pgs.

Chinese Office Action dated Aug. 25, 2021, in connection with corresponding CN Application No. 201680083583.6 (12 pp., including machine-generated English translation).

* cited by examiner

Surface curvature : small
Laplace pressure : small

CELL CULTURE VESSEL

FIELD

The present invention relates to a cell culture container in which a well for culturing cells is provided therein, and the well is immersed in a culture solution to culture a cell cluster.

BACKGROUND

A cell culture plate in which microwells (hereinafter simply called as wells) for culturing a cell cluster are formed in a plate has been proposed and put to practical use. As a cell culture plate, in addition to a single hole plate, there are multiwell plates having a plurality of wells such as 6 holes or 24 holes (see, for example, Patent Document 1 and Patent Document 2). In addition, there are cell culture plates with various wells of shape and size, such as circular wells and square wells, those with which wells are communicated, and those with through-holes at the bottom of wells.

When culturing a cell cluster using such a cell culture plate, the cell culture plate is placed at the bottom of a container (storage container) for storing a culture solution for culturing cells, and the cells are seeded in each well. The cells seeded in each well settle in the microwells and form a cluster in each well. By using a cell culture plate provided with a plurality of wells having uniform size, it is possible to efficiently prepare a cell cluster having uniform size.

Patent Document 1: Japanese Patent Laid-open Publication No. 2010-022275

Patent Document 2: Japanese Patent Laid-open Publication No. 2014-147342

SUMMARY

When culturing a cell cluster on a cell culture plate, it is necessary to replace the culture solution in the storage container. In replacement of the culture solution, it is common to manually perform the operation of firstly inclining the storage container with respect to the culture solution in the storage container or sucking it with a nozzle and then injecting the new culture solution into the storage container.

However, since there is a problem that the cell cluster collapses due to the flow of the culture solution at the time of injection of the culture solution, or comes out of the wells, it is necessary to inject the culture solution into the storage container at a constant and slow flow velocity. Furthermore, there is a problem that the cell cluster is removed from the well together with the old culture solution when the culture solution is discarded. Therefore, it is necessary to slowly and carefully perform replacement of the culture solution, and it takes a long time to replace the culture solution, thus there has been a problem that it is difficult to culture a large amount of cell cluster on many cell culture plates at the same time.

Thus, an object of the present invention is to facilitate replacement of a culture solution.

A cell culture container according to the present invention includes a storage container, a cell culture area, a culture solution supply unit, a discharge unit, and a rectification unit. The storage container stores a culture solution. The cell culture area is an area provided in a storage container for culturing cells. The culture solution supply unit supplies a culture solution to the cell culture area at a flow rate equal to or less than a predetermined flow rate. The discharge unit discharges the culture solution in the culture area to the outside of the storage container. In the rectification unit, a plurality of outflow ports are uniformly arranged in a direction perpendicular to the flow direction of the culture solution from the culture solution supply unit to the discharge unit.

The culture container may be an airtight container specified in the Japanese Pharmacopoeia. More specifically, it is a container that prevents infiltration of solids and liquids during normal handling, transportation and storage, and the outflow of the contents, and is a container that ensures ventilation for culturing. This makes it possible to maintain a safe culture environment more easily at the time of culture, open the airtight container only at the initial stage of replacement of the medium, remove the waste medium, and add fresh medium.

If necessary, it may be a sealed container specified in the Japanese Pharmacopoeia. When replacing the medium in the sealed container, it is further preferable to create a communication path so as not to cause an imbalance in pressure due to a change in the liquid amount of the culture solution supply unit or the discharge unit, or perform treatment such as opening the sealed container and flowing a gas.

Here, the "predetermined flow rate" that is the culture solution supply flow rate of the culture solution supply unit refers to a flow rate in which the cells retained in the cell culture area are not rolled up or flowed by the flow of the culture solution, and a laminar flow is generated in the cell culture area. Such a flow rate is, for example, a flow rate of 2 mL/min or less.

The discharge unit preferably has a discharge port for discharging a liquid in the storage container to the outside of the storage container and a weir provided higher than the height of the upper surface of the cell culture unit in the cell culture area, and is configured so that only a liquid that flows over the weir is guided to the discharge port. Then, while the liquid surface height of the culture solution in the culture solution supply unit is maintained higher than the height of the upper surface of the cell culture unit, the old culture solution swept away by the new culture solution supplied to the cell culture area by the culture solution supply unit is automatically discarded from the discharge port to the outside of the storage container. By these actions, replacement work of the culture solution in the storage container is facilitated, and it is possible to prevent the cells retained in the cell culture area from getting out of the wells or being discarded together with the old culture solution.

The culture solution supply unit may have a culture solution reservoir for storing a culture solution above the storage container and supply the culture solution stored in the culture solution reservoir by the own weight of the culture solution in the culture solution reservoir. Then, the configuration of the cell culture container can be simplified. Then, simply by placing a culture solution in the culture solution reservoir, the culture solution is automatically supplied into the storage container at a flow rate equal to or less than the predetermined flow rate by the own weight of the culture solution in the culture solution reservoir, so that the replacement work of the culture solution is facilitated.

Incidentally, when the culture solution flows over the weir, the culture solution rises at the upper end of the weir due to the surface tension of the culture solution, and the liquid surface height of the culture solution becomes higher than the height of the weir. This is because when the culture solution rises at the upper end of the weir, a pressure difference called Laplace pressure is generated across the liquid surface of the culture solution, and when the Laplace pressure cannot support the mass of the culture solution, the weir breaks down and the culture solution flows over the weir.

The magnitude of the Laplace pressure ΔP generated in the culture solution is expressed as the product of the surface tension and the surface curvature of the liquid surface at that point, as shown in the formula (1). The surface curvature is the sum of the curvatures of the sections when the curved surface is cut in two directions orthogonal to each other. In the formula (1), γ is the surface tension and is a variable specific to the liquid. $1/R_1$ is the curvature of the section when the liquid surface is cut in the vertical direction, and $1/R_2$ is the curvature of the section when the liquid surface is cut in the horizontal direction.

$$\Delta P=\gamma(1/R_1+1/R_2) \quad (1)$$

From the above formula (1), it is understood that the magnitude of the Laplace pressure ΔP varies depending on the planar shape of the weir. For example, in the case where the weir has a plate shape and the planar shape is linear, since the section of the liquid surface when cutting the culture solution raised in the weir shape in the horizontal direction is also a linear shape, $1/R_2$ is always 0. Therefore, the Laplace pressure ΔP is expressed as:

$$\Delta P=\gamma(1/R_1+0) \quad (2).$$

When the liquid surface rises and the water pressure due to gravity increases, the shape of the liquid surface changes so as to balance it, and the curvature $1/R_1$ increases. When the liquid surface protrudes to the downstream side of the weir and the curvature $1/R_1$ takes the maximum value, the Laplace pressure ΔP loses the gravity and the dam breaks down, and the culture solution flows over the weir.

In addition, $1/R_2$ is always negative when the planar shape of the weir is curved in a convex shape in a direction opposite to the flow direction of the culture solution, and the Laplace pressure ΔP becomes small as compared to the case where the planar shape of the weir is linear. As the Laplace pressure ΔP decreases, the liquid surface height of the culture solution rising on the weir also becomes lower, thus the culture solution easily flows over the weir to be guided to the discharge flow path. As the culture solution easily flows over the weir to be guided to the discharge flow path, the old culture solution is smoothly discarded through the discharge flow path, thus the replacement of the culture solution in the storage container can be smoothly performed.

From the above, in the cell culture container according to the present invention, it is preferable that the weir provided in the discharge unit has a portion in which the planar shape at the top end is curved in a convex shape toward the cell culture area side. The fact that the planar shape of the weir has a portion curved in a convex shape toward the cell culture area side means that a portion that "is curved in a convex shape in a direction opposite to the flow direction of the culture solution" is provided on the planar shape of the weir. The culture solution passes through the cell culture area and reaches the discharge unit. Therefore, in the portion of the weir in which the planar shape is curved in a convex shape toward the cell culture area side, the Laplace pressure ΔP becomes smaller than in the case where the planar shape of the weir is linear, the culture solution easily flows over the weir to be guided to the discharge flow path. As a result, the replacement of the culture solution in the storage container is smoothly performed.

Example of a preferred embodiment of the above case include an embodiment in which the planar shape of the weir is an annular shape, and the discharge port is provided inside the weir. That is, at least the upper end portion of the weir has a circular pipe shape. When the curvature $1/R_2$ at an arbitrary point of the culture solution going to flow over the weir is D, the radius of curvature of the weir is D, and the horizontal distance from the edge of the opening of the weir upper end at that point is r, it can be expressed as:

$$1/R_2=-(1/(D+r))<0 \quad (3)$$

and is constant. Therefore, the Laplace pressure ΔP at an arbitrary point is expressed as:

$$\Delta P=\gamma(1/R_1-1/(D+r)) \quad (4).$$

From the above formula (4), it can be seen that the Laplace pressure ΔP decreases as the outer diameter D of the upper end portion of the weir of a circular pipe shape becomes smaller.

In the case where the planar shape of the weir is formed into an annular shape, it is preferable that the discharge port is an upper end of a downwardly extending discharge flow path, the discharge flow path has a capillary portion having an inner diameter of 2 mm or less and a hydrophilic inner surface, and the capillary portion communicates with the discharge port. Then, the culture solution flowing over the weir is drawn into the discharge flow path by capillary force, so that the old culture solution can be discarded more smoothly.

Furthermore, a waste liquid reservoir for receiving the liquid discharged to the outside of the storage container through the discharge flow path is provided below the storage container, and when the discharge flow path extends vertically downward from the inside of the storage container and drips the waste liquid to the waste liquid reservoir, it is preferable that the inner diameter of the capillary portion increases as it goes downward. When the inner diameter of the capillary portion of the discharge flow path is small, it is considered that the liquid is likely to stay in the capillary portion and the culture solution cannot be discarded smoothly. Such an inconvenience can be alleviated by increasing the inner diameter of the capillary portion of the discharge flow path as it goes downward.

In addition, a droplet of the culture solution is formed at the lower end of the discharge flow path, and when the outer diameter of the droplet is small, the Laplace pressure generated in the droplet becomes large, and the culture solution is less likely to be dropped from the discharge flow path to the waste liquid reservoir. Therefore, it is preferable that the length and the inner diameter of the lower end of the capillary portion are set so that the Laplace pressure generated on the liquid surface formed at the lower end of the capillary portion is smaller than the gravity of the liquid in the capillary portion. Then, the culture solution drawn into the capillary portion is likely to descend by the own weight, and it is possible to prevent the culture solution from clogging in the capillary portion.

The discharge flow path preferably has, below the capillary portion, an enlarged portion having an inner diameter larger than the inner diameter of the lower end of the capillary portion and having an open lower portion. Then, the outer diameter of the liquid surface formed at the downstream end of the discharge flow path becomes large, and the Laplace pressure generated on the liquid surface of the culture solution at the lower end of the discharge flow path decreases. As a result, the culture solution is likely to be dropped from the lower end of the discharge flow path to the waste liquid reservoir, and discard of the culture solution is promoted.

It is preferable that a cross section of the upper end portion of the weir has an acute angle shape converging upward, that is, there is no flat surface at the upper end portion of the weir, and the outer diameter of the upper end portion of the weir is very close to the inner diameter of the inside thereof. As a result, the culture solution is less likely to rise on the weir, and the discard of the culture solution is more smoothed. Further, by setting the outer diameter of the weir upper end portion closer to its inner diameter to 2.5 mm or less, the Laplace pressure ΔP can be reduced, and when the liquid surface attempts to protrude inward from the edge of the weir, the liquid surfaces come into contact with each other on the weir and flow into the discharge flow path, so that the maximum value that $1/R_1$ in the formula (4) can take becomes even smaller, and the discard of the culture solution flowing over the weir is more smoothed.

Also, examples of a preferred embodiment of the rectification unit include those including a rectification path in which a plurality of flow paths parallel to a solvent flow direction from a culture solution supply unit side to a discharge unit side of the cell culture area are uniformly arranged in a direction perpendicular to the solvent flow direction in the horizontal plane.

The new culture solution supplied to the storage container is likely to flow on the surface layer side of the culture solution stored in the storage container, and the culture solution located on the bottom surface side of the storage container is less likely to be replaced while the culture solution on the surface layer side is replaced. Therefore, it is preferable that each of the flow paths constituting the rectification path is configured to block the liquid on the surface layer side in the storage container and pass the liquid on the bottom layer side of the storage container. Then, since the new culture solution is supplied from the vicinity of the bottom surface of the storage container to the cell culture area, the culture solution located on the bottom surface side of the storage container is also likely to be replaced.

Since the cell culture container according to the present invention includes a culture solution supply unit for supplying a culture solution into a storage container from one end side of a cell culture area at a flow rate equal to or less than a predetermined flow rate, it is possible to supply a new culture solution to the cell culture area at a flow rate equal to or less than a predetermined flow rate. Furthermore, since it has a rectification unit in which a plurality of outflow ports are uniformly arranged in a direction perpendicular to the flow direction of the culture solution from the culture solution supply unit to a discharge unit, the flow velocity distribution of a new culture solution supplied by the culture solution supply unit in the plane of the cell culture area becomes uniform, and the culture solution in the entire cell culture area can be easily and uniformly replaced with the new culture solution.

DETAILED DESCRIPTION

An embodiment of a cell culture device according to the present invention will be described with reference to the drawings.

Figure 1:
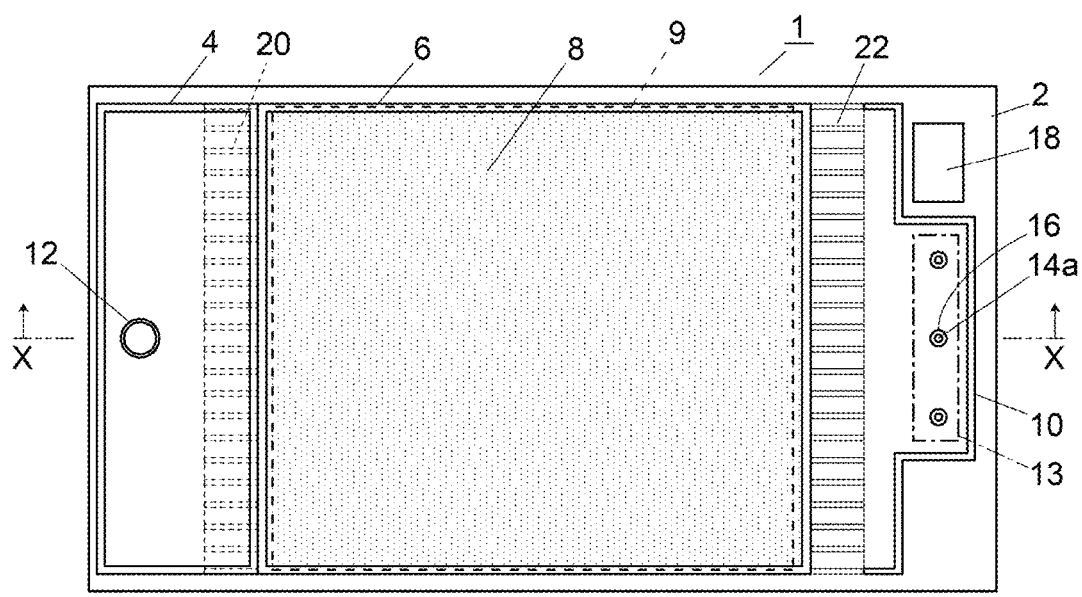
FIG. 1 is a plan view showing an embodiment of a cell culture container.
Figure 2:
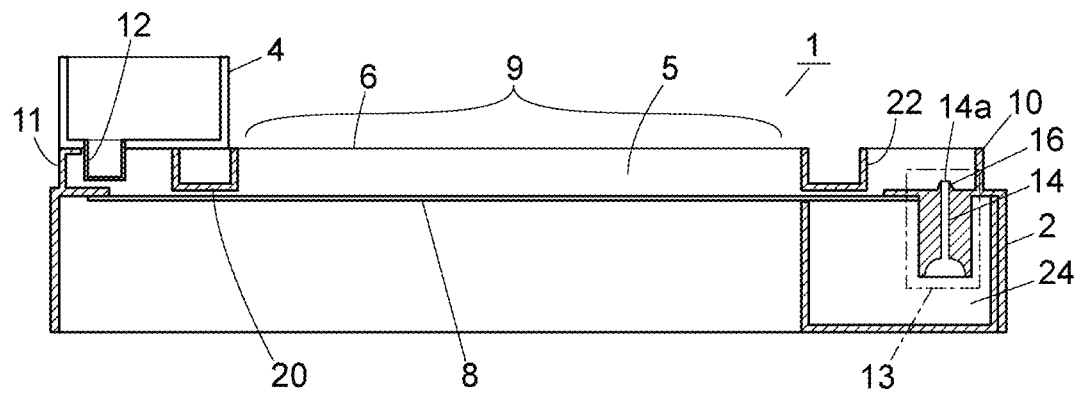
FIG. 2 is a cross-sectional view taken along line X-X of FIG. 1.

As shown in FIGS. 1 and 2, a cell culture container 1 includes a frame 2, a culture solution reservoir 4, a dimple membrane 8, and a waste liquid reservoir 24. The dimple membrane 8 is a member on the plate, and a plurality of microwells for culturing cells are arranged on one side. The dimple membrane 8 is attached to the frame 2 in a state where the surface on the side where the microwells are arranged is on the upper side.

Side walls 6, 10, 11 are provided on the upper surface side of the frame 2, and the dimple membrane 8 attached to the frame 2 and the side walls 6, 10, 11 form a storage container 5 of a culture solution with the dimple membrane 8 as the bottom surface. The dimple membrane 8 has microwells in a plane between a rectification path 20 and a rectification path 22, which will be described later. In the storage container 5 formed by the dimple membrane 8 and the side walls 6, 10, the area of the dimple membrane 8 surrounded by a broken line where the microwells are arranged is called as a cell culture area 9.

In this embodiment, the cell culture area 9 has a rectangular shape, but it may have a circular shape, an oval shape or another shape. In addition, in this embodiment, a plurality of microwells are arranged in the cell culture area 9, but the wells are not necessarily need to be arranged, as long as they can be cultured by retaining cells.

In this embodiment, the upper surface of the storage container 5 is opened, but the upper surface of the storage container 5 does not necessarily need to be opened, and may be sealed to be an airtight container. This makes it possible to maintain a safe culture environment more easily at the time of culture, open the airtight container only at the initial stage of replacement of the medium, remove the waste medium, and add fresh medium.

The culture solution reservoir 4 is attached to the upper surface of the end portion on one end side (left side in the figures) of the frame 2. The culture solution reservoir 4 is a container with an open top, and a pin 12 protruding downward is provided on the bottom surface thereof. The culture solution reservoir 4 and the pin 12 constitute a culture solution supply unit for supplying a new culture solution to the cell culture area 9 at a flow rate equal to or less than a predetermined flow rate.

Figure 3A:
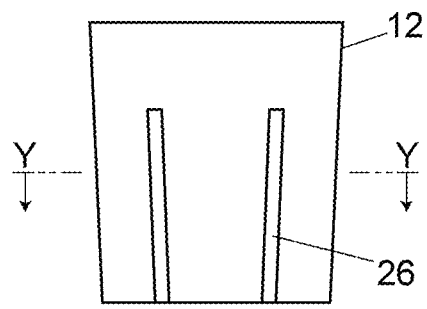
FIG. 3A is a front view showing a structure of a culture solution supply unit of the same embodiment.
Figure 3B:
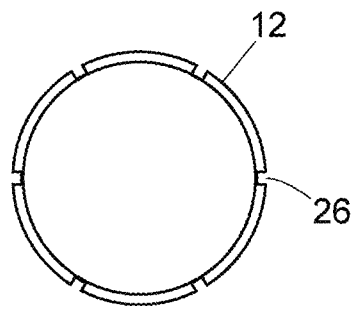
FIG. 3B is a cross-sectional view taken along line Y-Y of FIG. 3A.

As shown in FIGS. 3A and 3B, the pin 12 has a plurality of grooves 26 on its outer peripheral surface. The outflow flow rate of the culture solution from the culture solution reservoir 4 is controlled by the pipeline resistance of the groove 26, and the relation of the following formula using the outflow flow rate as Q is established. Here, n is the number of grooves 26, L is the length of the groove 26, $\mu$ is the viscosity coefficient of the culture solution, p is the density of the culture solution, a is the length of one side of the flow path cross section, g is the gravitational acceleration, and h is the liquid surface height of the culture solution in the reservoir.

$$Q = n \frac{1}{48} \frac{a^4}{L\mu} \rho g h$$

In this embodiment, six grooves 26 having a length dimension of 5 mm, a thickness dimension of 0.35 mm, and a width dimension of 0.35 mm are provided. In this case, when the culture solution is accumulated up to the upper end of the culture solution reservoir 4 (the height from the bottom surface is 15 mm), the flow rate Q becomes the maximum at 1.2 mL/min. With this flow rate, the average flow velocity of the culture solution in the cell culture area 9 is about 0.16 mm/s, and the cells retained in the microwells do not be rolled up by the flow of the culture solution. In the configuration of this embodiment, when the supply flow rate of the culture solution from the culture solution reservoir 4 is 2 mL/min or less, the cells retained in the microwell do not be rolled up.

Figure 10:
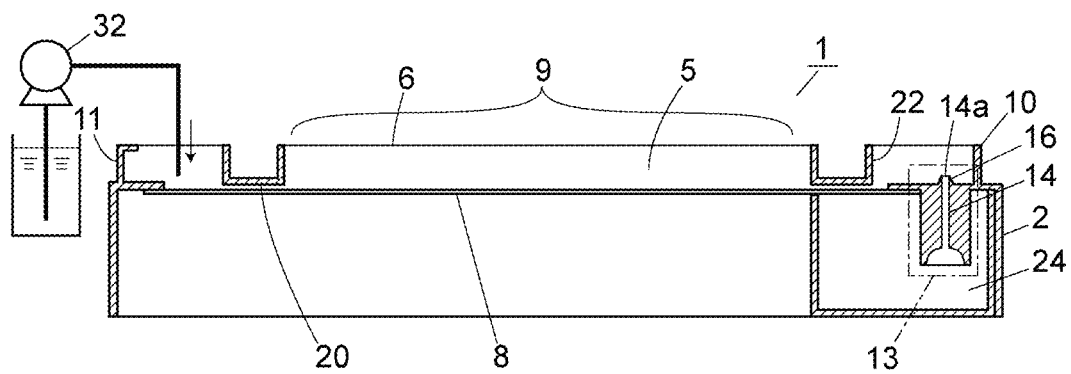
FIG. 10 is a plan view showing another embodiment of a cell culture container.

Meanwhile, a mechanism for supplying the culture solution to the culture solution reservoir 4 at a constant flow rate may be provided so that the flow velocity of the culture solution flowing out from the culture solution reservoir 4 is constant. Also, a mechanism for supplying the culture solution at a constant flow rate, such as a liquid transfer pump 32 shown in FIG. 10, may be provided, in place of the culture solution reservoir 4, and the culture solution may be directly supplied from this mechanism into the storage container 5 at a constant flow rate.

Referring back to FIGS. 1 and 2, a discharge unit 13 is provided at the end portion on the other end side (right side in the figures) of the frame 2, and the waste liquid reservoir 24 is provided below the discharge unit 13. The discharge unit 13 has a discharge flow path 14 therein extending vertically downward. An opening 14a at the upper end of the discharge flow path 14 forms a discharge port for discharging the culture solution in the storage container 5 through the discharge flow path 14. Hereinafter, the opening 14a at the upper end of the discharge flow path 14 is called as "discharge port 14a". A peripheral edge portion 16 of the discharge port 14a raises more than its surroundings and forms a weir for maintaining the liquid surface height of the culture solution in the storage container 5 at a constant height. Hereinafter, the peripheral edge portion 16 of the discharge port 14a is called as a "weir 16". The discharge unit 13 discharges only the culture solution flowing over the weir 16 to the waste liquid reservoir 24 through the discharge flow path 14.

Figure 5:
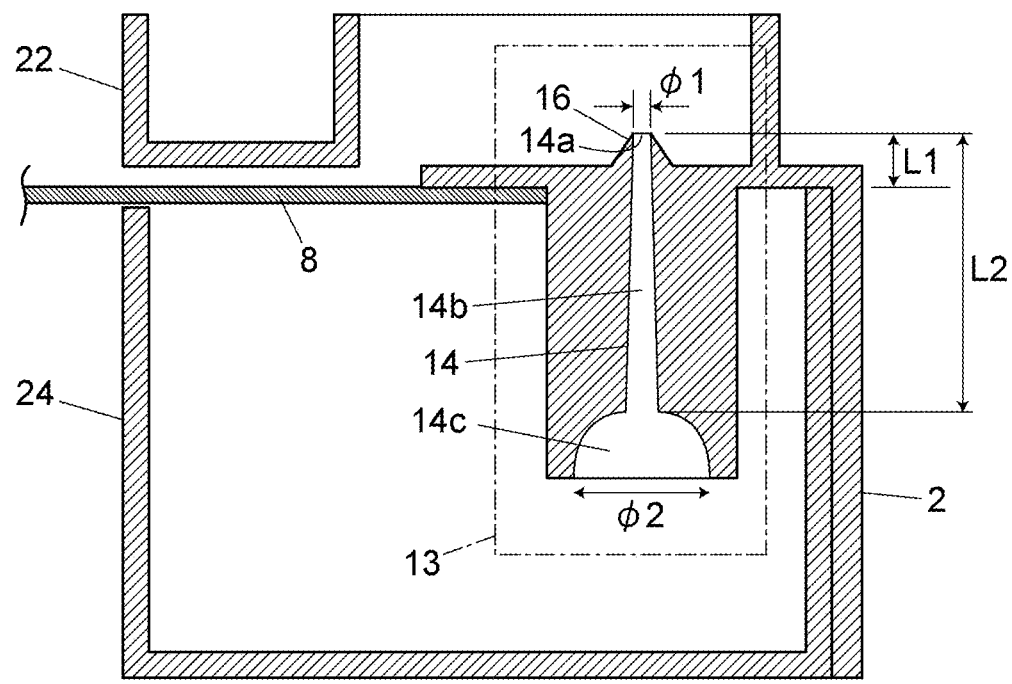
FIG. 5 is a cross-sectional view for explaining a structure of a discharge unit of the same embodiment.
Figure 6A:
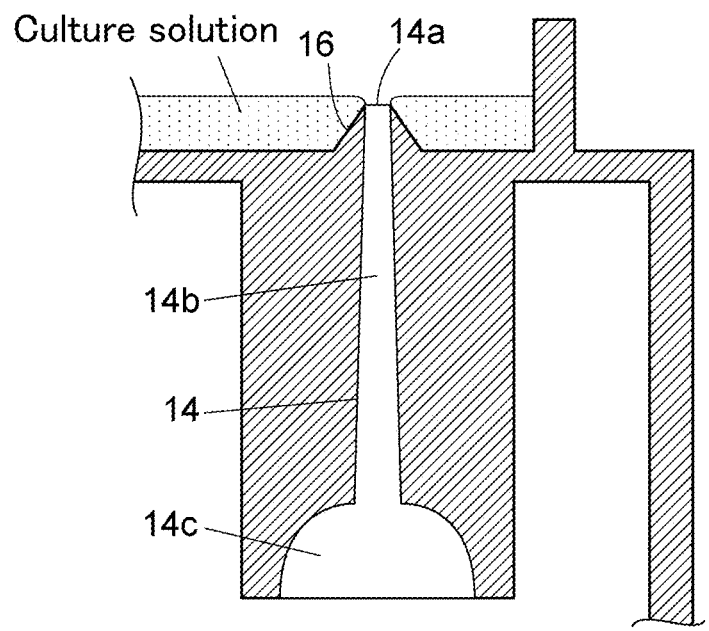
FIG. 6A is a cross-sectional view showing a state in which a culture solution rises on a weir of a discharge unit.
Figure 7A:
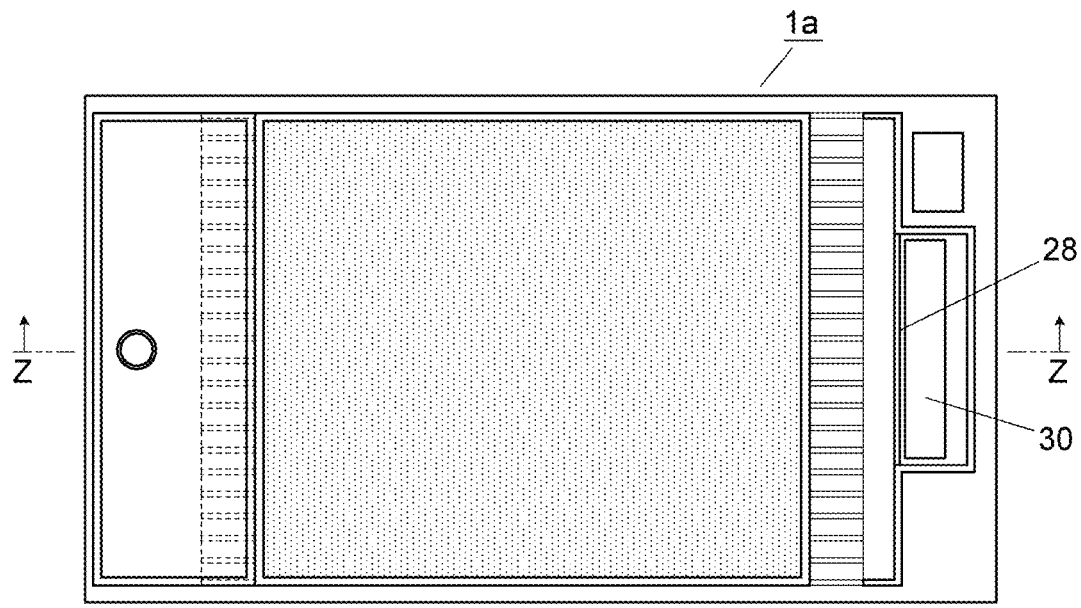
FIG. 7A is a plan view showing another embodiment of a cell culture container.
Figure 7B:
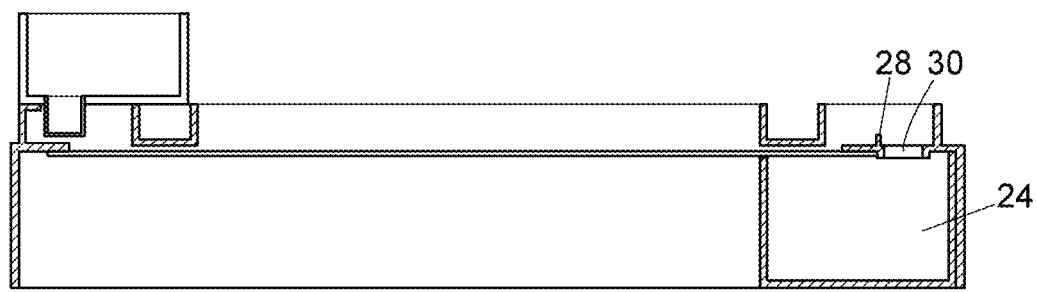
FIG. 7B is a cross-sectional view taken along line Z-Z of FIG. 7A.
Figure 7C:
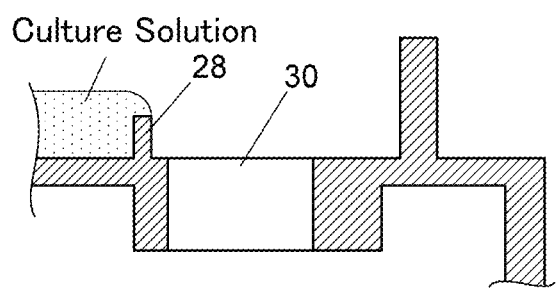
FIG. 7C is a cross-sectional view showing a state in which a culture solution rises on a weir of a discharge unit.

As shown in FIG. 5, the discharge flow path 14 has a capillary portion 14b and an enlarged portion 14c. The upper end of the capillary portion 14b communicates with the discharge port 14a. The weir 16 around the discharge port 14a has a circular pipe shape and has a tapered shape which does not have a flat surface at its upper end so that the outer diameter of the upper end portion is substantially the same as inner diameter $\phi 1$ of the discharge port 14a. As a result, the Laplace pressure generated in the culture solution flowing over the weir 16 decreases, and as shown in FIG. 6A, although the culture solution rises on the weir 16, the liquid surface height becomes small as compared to the case of a plate-like weir 28 as shown in FIGS. 7A to 7C. As a result, the culture solution exceeding the height L1 of the weir 16 from the surface of the dimple membrane 8 is easily discharged through the discharge flow path 14b. L1 is, for example, 2 mm.

Figure 6B:
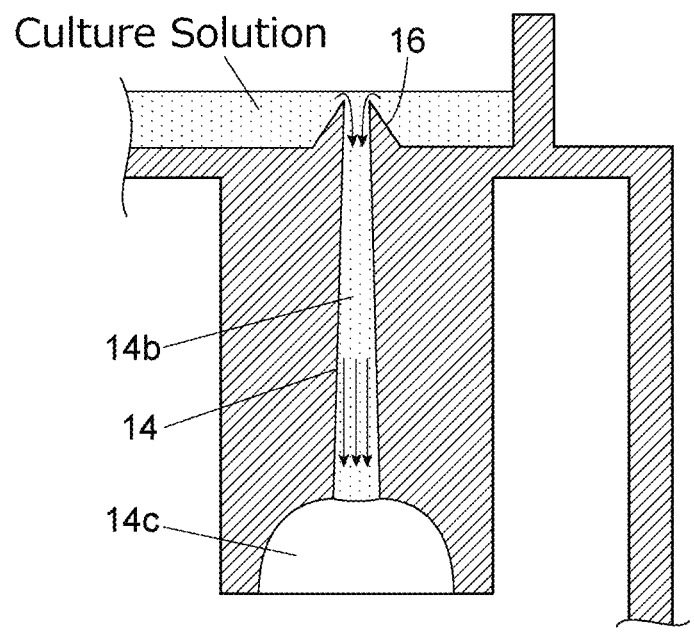
FIG. 6B is a cross-sectional view showing a state in which a culture solution is drawn into a capillary portion of a discharge flow path.

Further, the capillary portion 14a of the discharge flow path 14 is formed to have an inner diameter such that the liquid is drawn into the inside by capillary force. As a result, when the culture solution faces the discharge port 14a, as shown in FIG. 6B, the culture solution is drawn into the capillary portion 14a by capillary force. The inner diameter of the capillary portion 14a is larger as it goes downward so that the culture solution drawn inside is less likely to clog in the middle. The inner diameter of the discharge port 14a is, for example, 1.1 mm.

Length L2 of the capillary portion 14b is designed so that the gravity of the culture solution in the capillary portion 14b is larger than the Laplace pressure generated on the liquid surface formed at the lower end of the capillary portion 14b. While the culture solution drawn into the capillary portion 14b tries to stay in the capillary portion 14b due to the Laplace pressure generated on the liquid surface at the lower end, the Laplace pressure cannot withstand the gravity of the culture solution in the capillary portion 14b and drops, then the culture solution is less likely to clog in the capillary portion 14b. L2 is, for example, 8 mm.

Figure 6C:
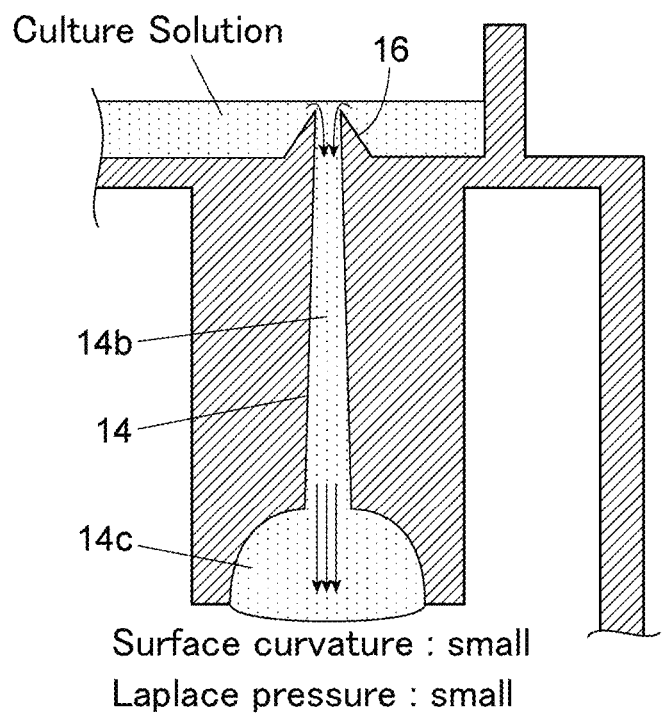
FIG. 6C is a cross-sectional view showing a state in which a culture solution reaches an enlarged portion of a discharge flow path.

An enlarged portion 14c is provided below the capillary portion 14a. Inner diameter $\phi 2$ of an opening portion is set such that the lower part of the enlarged portion 14c opens and the Laplace pressure generated on the liquid surface of the culture solution formed in the opening is smaller than the water pressure of the culture solution in the enlarged portion 14c. That is, when the opening area of the lower end portion of the discharge flow path 14 is increased, as shown in FIG. 6C, the surface curvature of the liquid surface of the culture solution formed therein also becomes small, and the Laplace pressure generated on the liquid surface also becomes small. $\phi 2$ is, for example, 4.8 mm.

As a result, when the liquid surface of the culture solution in the storage container 5 exceeds the weir 16, the culture solution is smoothly discharged to the waste liquid reservoir 24 through the discharge flow path 14, and the culture solution can be stably replaced.

Figure 8A:
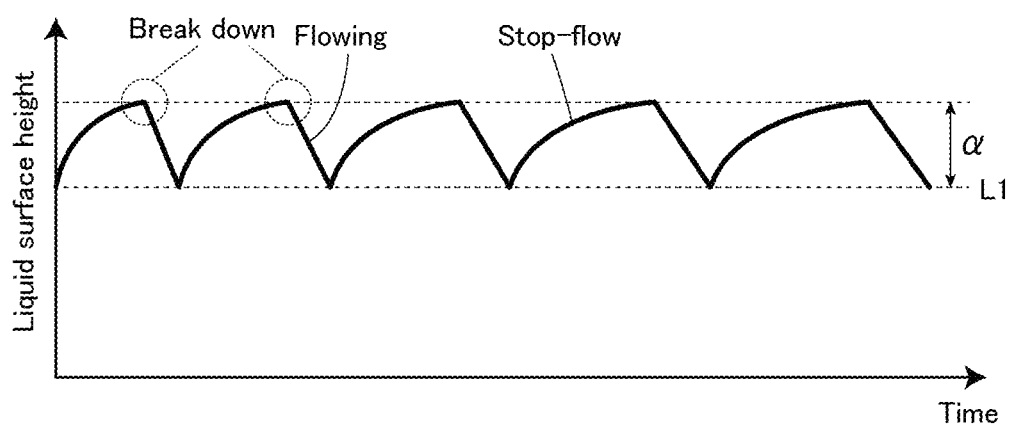
FIG. 8A is a graph showing an example of temporal change in liquid surface height in a storage container when a weir of a discharge unit is formed into a plate shape.

Here, as shown in FIGS. 7A to 7C, when the weir 28 for maintaining the liquid surface height of the culture solution in the storage container 5 constant is provided, and a discharge port 30 for guiding the culture solution flowing over the weir 28 to the waste liquid reservoir 24 is provided on the downstream side of the weir 28, as shown in FIG. 8A, outflow of the culture solution intermittently occurs, due to the Laplace pressure generated on the liquid surface when the culture solution flows over the weir 28. That is, even when the liquid surface height of the culture solution reaches the height (L1) of the weir 28, the culture solution rises at the edge of the weir 28 due to the Laplace pressure by surface amount force and the liquid surface rises. When the Laplace pressure cannot withstand the water pressure of the culture solution, the weir breaks down, the culture solution flows out and the liquid surface height drops, and when the liquid surface reaches the height of the weir 28, the outflow stops. Then, once the outflow of the culture solution stops, the culture solution is blocked again by the Laplace pressure at the edge of the weir 28, and when the liquid surface height rises to reach a certain height (L1+α), the weir breaks down.

The cell culture container according to the present invention also includes a cell culture container 1a as shown in FIGS. 7A to 7C, and since the planar shape of the weir 28 of the cell culture container 1a is linear, relatively large Laplace pressure is generated on the liquid surface of the culture solution at the edge of the weir 28 and height α of the liquid surface which is higher than the weir 28 increases.

Figure 8B:
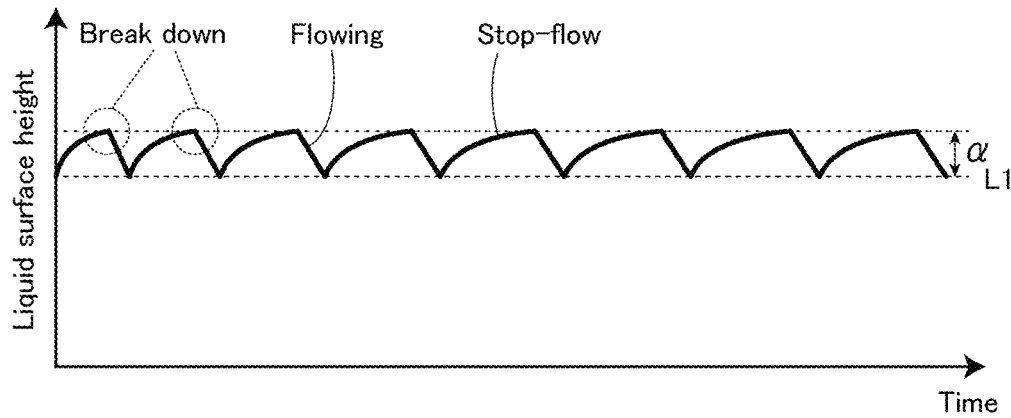
FIG. 8B is a graph showing an example of temporal change in liquid surface height in a storage container when a weir of a discharge unit is formed in a circular tube shape.

In contrast, since the weir 16 in the cell culture container 1 described with reference to FIGS. 1 to 6C has a circular pipe shape and no flat surface is present at the upper end thereof, the Laplace pressure becomes smaller than the linear weir 28. As a result, as shown in FIG. 8B, the required liquid surface rise height α decreases until the weir 16 breaks down and the culture solution is drawn into the discharge flow path 14, the outflow cycle of the culture solution is discharged to the waste liquid reservoir 24 is shortened, and the flow of the culture solution in the cell culture area 9 also becomes continuous. Therefore, replacement of the culture solution in the cell culture area 9 can be stably performed.

As mentioned above, the Laplace pressure ΔP generated on the liquid surface when flowing over the weir is expressed as:

$$\Delta P = \gamma(1/R_1 + 1/R_2).$$

In order to reduce the Laplace pressure ΔP, the curvature $1/R_2$ of the section when the liquid surface is cut in the horizontal direction should be minus. Therefore, for example, the planar shape of the weir 1a of the cell culture container 1a in FIGS. 7A to 7C may have a curved portion protruding toward the cell culture area 9 side.

Referring back to FIGS. 1 and 2, the frame 2 includes an opening portion 18 for sucking the old culture solution in the waste liquid reservoir 24 by a suction nozzle, at a position above the waste liquid reservoir 24 and different from the discharge unit 13. Thus, it is possible to collect the old culture solution without tilting the cell culture container 1 and removing the waste liquid reservoir 24.

A rectification path 20 for uniformizing the flow velocity of the culture solution flowing out of the pin 12 on one end side (left side in the figures) from the cell culture area 9 of the storage container 5 in the plane of the cell culture area 9 is provided. The rectification path 20 is a path in which a plurality of flow paths parallel to the flow direction (the left-right direction in the figures) of the culture solution flowing from the pin 12 toward the discharge unit 13 are uniformly arranged in a direction perpendicular to the flow direction of the culture solution in the horizontal plane (a vertical direction in FIG. 1, a direction perpendicular to the paper surface in FIG. 2). In this embodiment, the rectification path 20 was constituted by 22 flow paths, and each flow path had a width of 2 mm, a height of 0.5 mm, and a length of 10 mm.

Figure 4:
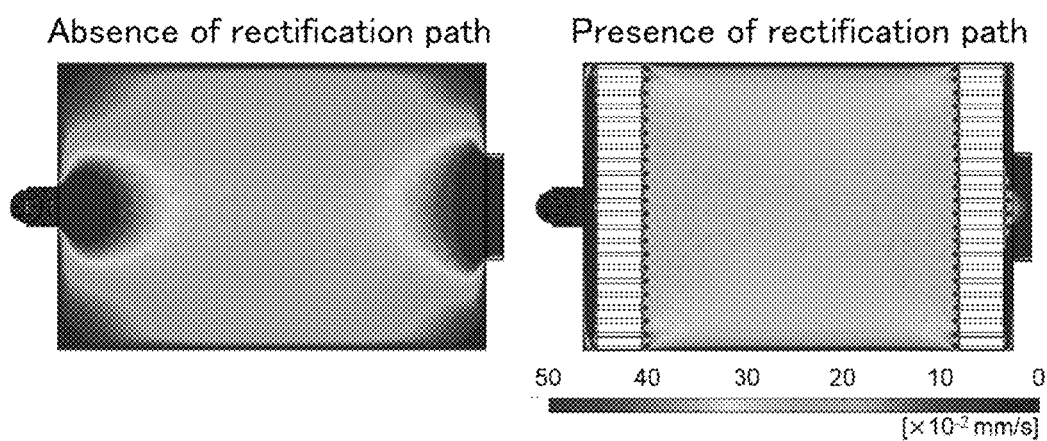
FIG. 4 is a view showing a result of examination of rectification effect by a rectification path. The diagram on the left side is a flow velocity distribution diagram in the case where a rectification path is not provided, and the diagram on the right side is a flow velocity distribution diagram in the case where a rectification path is provided.

Also on the other end side (right side in the figures) of the cell culture area 9 of the storage container 5, a rectification path 22 having the same configuration as the rectification path 20 is provided. Simulation results of the rectification effect of these rectification paths 20, 22 are shown in FIG. 4. This simulation was performed using physical simulation software COMSOL Multiphysics. As shown in FIG. 4, in the absence of the rectification paths 20, 22, the flow velocity of the culture solution is fast near the pin 12 and near the discharge unit 13, and the distribution largely varies within the plane. On the other hand, when the rectification paths 20, 22 were provided, the in-plane flow velocity distribution became uniform except for the vicinity of the upstream end and the downstream end of the cell culture area 9. When the in-plane flow velocity distribution becomes uniform, the old culture solution is unlikely to be left behind, so that it is possible to replace more old culture solution with equal amounts of new culture solution.

In addition, the culture solution in the storage container 5 takes the flow velocity distribution that it is the fastest in the vicinity of the liquid surface and the slowest in the vicinity of the bottom surface. This relative flow velocity distribution itself does not depend on the average flow velocity. In the case where the average flow velocity is fast (for example, 10 mL/min or more), the old culture solution is immediately replaced with a new culture solution in the vicinity of the liquid surface, but almost no flow occurs in the vicinity of the bottom surface, so that the old culture solution is left behind. Therefore, the amount of old culture solution to be removed is small relative to the amount of new culture solution flowing into the cell culture area 9. Therefore, only when the culture solution is flowed in one direction, the old culture solution stagnates on the deep layer side, and it is difficult to efficiently replace the old culture solution in the vicinity of the cells retained in the well with a new culture solution.

On the other hand, each flow path forming the rectification path 20 blocks the culture solution on the surface layer side and flows only on the deep layer side. By supplying a new culture solution from the deep layer side to the cell culture area 9 by the rectification path 20, replacement of the older culture solution on the deep layer side is also promoted.

Further, the flow rate of the new culture solution supplied to the storage container 5 through the pin 12 is very small as 1.2 mL/min at the maximum. Due to this delay in average flow velocity, a new mobile phase flowing on the surface layer side and an old culture solution existing near the bottom surface are mixed by molecular diffusion, and more old culture solution is replaced.

In addition, even when the rectification path 20 is not provided, a plurality of outflow ports through which the culture solution of the culture solution reservoir 4 flows out are uniformly arranged in a direction perpendicular to the flow direction of the culture solution (a vertical direction in FIG. 1), whereby it is possible to obtain the same effect as in the case where the rectification path 20 is provided.

Figure 9:
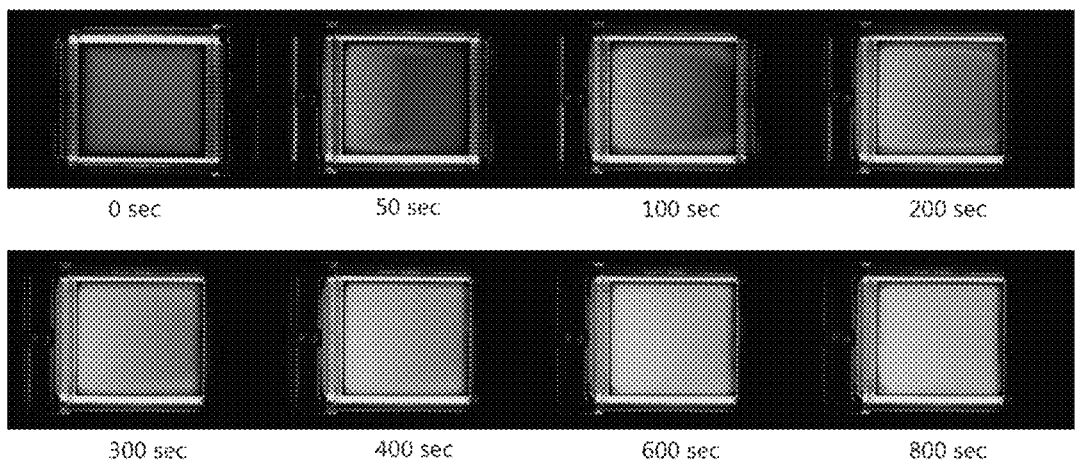
FIG. 9 is an image diagram showing a replacement state of a culture solution in a storage container for each elapsed time.

Next, the results of experiments conducted on replacement of the culture solution using the cell culture container 1 will be described with reference to FIG. 9. In this experiment, using an aqueous dye solution as an alternative to the old culture solution, and using water as an alternative to the new culture solution, rhodamine B (Sigma-Aldrich Corporation) was used as a dye. The state in which the rhodamine B aqueous solution in the cell culture area 9 was replaced with water flowing out of the culture solution reservoir 4 was observed.

The water poured into the reservoir at time 0 seconds flowed into the cell culture area 9 over about 800 seconds, and the rhodamine aqueous solution was accumulated in the waste liquid reservoir 24. FIG. 9 is images extracting only a G (green) channel out of RGB from the photographed images taken by a single lens reflex camera from the upper side while irradiating the cell culture area during experiment with light from the lower side of the plate with the LED surface light source. The shutter speed was 1/20 seconds, and the aperture was F22. On the G channel image, red rhodamine B appears black.

From these images, it can be confirmed that the rhodamine B aqueous solution in the cell culture area is replaced with water from the culture solution reservoir 4, whereby the black color gradually pales.

In this manner, in the cell culture container 1 described above, simply by adding a necessary amount of a new culture solution to the culture solution reservoir 4, the culture solution in the culture solution reservoir 4 flows out of the culture solution reservoir 4 by its own weight, and flows into the cell culture area 9 with a gentle flow rate so as not to wind up the cells contained in each well of the cell culture area 9. Then, the new culture solution flowing into the cell culture area 9 pushes the old culture solution to the discharge unit 13 side, and the old culture solution is discharged to the waste liquid reservoir 24 through the discharge flow path 14. As a result, the replacement work of the culture solution becomes very simple, and at the same time, it is also possible to replace the culture solution of a plurality of cell culture containers.

The invention claimed is:

1. A cell culture container comprising:
   a storage container for storing a culture solution;
   a cell culture area provided in the storage container for culturing cells;
   a culture solution supply unit for supplying the culture solution to the cell culture area at a flow rate equal to or less than a predetermined flow rate; and
   a discharge unit for discharging the culture solution in the cell culture area to the outside of the storage container,
   wherein the discharge unit has a discharge port for discharging a liquid in the storage container to the outside of the storage container and a weir provided higher than the height of an upper surface of a cell culture unit provided in the cell culture area, the discharge port is provided at an upper end portion of the weir, and the discharge unit is configured so that only a liquid that flows over the weir is guided to the discharge port, and
   wherein a cross section of the upper end portion of the weir has an acute angle shape converging upward toward the discharge port.

2. The cell culture container according to claim 1, the cell culture container comprises a rectification unit in which a plurality of outflow ports are uniformly arranged in a direction perpendicular to a flow direction of the culture solution from the culture solution supply unit to the discharge unit.

3. The cell culture container according to claim 2, wherein the cell culture area comprises a culture solution supply unit side at which the culture solution from the culture solution supply unit is supplied and a discharge unit side at which the culture solution is discarded to the discharge unit, and
   the rectification unit comprises a rectification path in which a plurality of flow paths parallel to a solvent flow direction from the culture solution supply unit side to the discharge unit side of the cell culture area are uniformly arranged in a direction perpendicular to the solvent flow direction in a horizontal plane.

4. The cell culture container according to claim 3, wherein each of the flow paths constituting the rectification path is configured to block the liquid on a surface layer side and pass the liquid on a deep layer side.

* * * * *